US009561011B2

(12) United States Patent
Arakita et al.

(10) Patent No.: US 9,561,011 B2
(45) Date of Patent: Feb. 7, 2017

(54) X-RAY CT APPARATUS, MEDICAL IMAGE PROCESSING APPARATUS AND MEDICAL IMAGE PROCESSING METHOD

(75) Inventors: Kazumasa Arakita, Nasushiobara (JP); Yoshihiro Ikeda, Sakura (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1226 days.

(21) Appl. No.: 12/560,047

(22) Filed: Sep. 15, 2009

(65) Prior Publication Data

US 2010/0067767 A1    Mar. 18, 2010

(30) Foreign Application Priority Data

Sep. 17, 2008    (JP) .................................. 2008-238588

(51) Int. Cl.
*A61B 5/055*    (2006.01)
*A61B 5/026*    (2006.01)
*A61B 6/00*    (2006.01)

(52) U.S. Cl.
CPC .............. *A61B 6/504* (2013.01); *A61B 6/507* (2013.01)

(58) Field of Classification Search
CPC ......... A61B 6/507; A61B 6/504; A61B 6/481; A61B 5/055; A61B 6/032; A61B 5/0263; A61B 6/501; A61B 6/5217; A61B 6/4441; A61B 8/481; A61B 5/026; A61B 6/486; A61B 6/503; A61B 6/5235

(Continued)

(56) References Cited

U.S. PATENT DOCUMENTS 6,516,214 B1 *   2/2003   Boas .................... A61B 5/0073
                                                      600/310
6,641,538 B2 *  11/2003   Nakaya et al. ............... 600/458

(Continued)

FOREIGN PATENT DOCUMENTS

EP          1604612 A1 * 12/2005
JP       2006-130129       5/2006
(Continued)

OTHER PUBLICATIONS

Miles, Kenneth A. , M.D. et al., "Application of CT in the Investigation of Angiogenesis in Oncology", XP 5307854A, Academic Radiology, vol. 7, No. 10, Oct. 1, 2000, pp. 840-850.*

(Continued)

*Primary Examiner* — Neal Sereboff
(74) *Attorney, Agent, or Firm* — Oblon, McClelland, Maier & Neustadt, L.L.P.

(57) ABSTRACT

An X-ray CT apparatus includes a perfusion data acquisition unit, a perfusion parameter calculating unit and a perfusion parameter display unit. The perfusion data acquisition unit generate perfusion data by exposing an X-ray to the object with injecting contrast medium. The perfusion parameter calculating unit calculates perfusion parameters corresponding to ROIs based on time variations in density of the contrast medium for the ROIs. The perfusion parameter display unit divides a period to be a calculation target of the time variations into plural time ranges and sequentially displays images each including the ROIs. The images correspond to the time ranges and mutually different time phases respectively and are masked so as to make only ROIs at which the perfusion parameters show values displayed.

9 Claims, 5 Drawing Sheets

(58) Field of Classification Search
USPC .... 600/435, 426, 427, 458, 504, 431; 378/4, 378/8, 91; 382/131, 128
See application file for complete search history.

(56) References Cited

U.S. PATENT DOCUMENTS

| | | | | |
|---|---|---|---|---|
| 7,069,068 | B1* | 6/2006 | Ostergaard | A61B 6/507 324/307 |
| 2003/0097076 | A1* | 5/2003 | Nambu et al. | 600/504 |
| 2003/0114759 | A1* | 6/2003 | Skyba | A61B 8/08 600/458 |
| 2004/0267113 | A1* | 12/2004 | Thomson | 600/427 |
| 2005/0277830 | A1* | 12/2005 | Ichihara | 600/425 |
| 2006/0241402 | A1* | 10/2006 | Ichihara | A61B 6/481 600/425 |
| 2007/0016016 | A1* | 1/2007 | Haras | G06K 9/3233 600/431 |
| 2007/0030946 | A1* | 2/2007 | Tsuyuki et al. | 378/8 |
| 2008/0107233 | A1* | 5/2008 | Sakaguchi | A61B 6/4233 378/91 |
| 2008/0194943 | A1* | 8/2008 | Lorenz | A61B 5/0263 600/419 |
| 2008/0232666 | A1* | 9/2008 | Rottger | 382/131 |
| 2008/0247503 | A1* | 10/2008 | Lauritsch et al. | 378/4 |
| 2008/0262344 | A1* | 10/2008 | Brummett | 600/426 |
| 2009/0028406 | A1* | 1/2009 | Arditi | A61B 8/06 382/131 |
| 2009/0129536 | A1* | 5/2009 | Ichihara | A61B 6/481 378/4 |
| 2009/0129649 | A1* | 5/2009 | Djeridane | G06T 7/0014 382/131 |
| 2009/0297008 | A1* | 12/2009 | Taxt et al. | 382/131 |

FOREIGN PATENT DOCUMENTS

| | | |
|---|---|---|
| JP | 2006-247388 | 9/2006 |
| JP | 2008-100121 | 5/2008 |
| WO | WO 2007132242 A1 * | 11/2007 |

OTHER PUBLICATIONS

George, Richard T. et al., "Multidetector Computer Tomography Myocardial Perfusion Imaging During Adenosine Stress", Journal of the American College of Cardiology, vol. 48, No. 1, 2006, pp. 153-160.*

Definition—corresponding as downloaded on Sep. 9, 2015.*

* cited by examiner

X-RAY CT APPARATUS, MEDICAL IMAGE PROCESSING APPARATUS AND MEDICAL IMAGE PROCESSING METHOD

BACKGROUND OF THE INVENTION

1. Field of the Invention

The present invention relates to an X-ray CT apparatus, and a medical image processing apparatus and a medical image processing method that generate and display information with time showing a result of blood flow perfusion analysis acquired from an object.

2. Description of the Related Art

Conventionally, a perfusion analysis of a blood flow in various organs of an object is performed using an image diagnostic apparatus such as an X-ray CT (computed tomography) apparatus, an MRI (magnetic resonance imaging) apparatus or a nuclear medicine diagnostic apparatus (see, for example, Japanese Publication of Patent Application No. 2006-247388). The conventional perfusion analysis is performed using data obtained with injecting a contrast medium or a tracer into an object. The perfusion analysis allows observing a dynamic state of a blood flow.

A color map is more often used as a display method of a result of the perfusion analysis. Observation that uses the color map is aggressively used in diagnosis of a blood flow dynamic state and a location of ischemia. Especially, the perfusion analysis in a vessel of a head or a tissue such as the heart or the liver sustained from vessels is a very significant analysis for understanding the function of the tissue.

FIG. 1 shows conventional graphs indicating TDCs (time density curves) of contrast medium obtained as a result of perfusion analysis. FIG. 2 is an image showing a method of displaying a perfusion analysis result obtained as the TDCs as shown in FIG. 1.

In each graph in FIG. 1, the ordinate axis denotes a CT value (HU: Hounsfield Unit) corresponding to a density of contrast medium injected into an object and the abscissa axis denotes time. The respective curves in FIG. 1 represent TDCs in respective ROIs (regions of interest) (ROI1, ROI2, ROI3, ... ).

In the conventional perfusion analysis, a TDC of each ROI as shown in FIG. 1 is produced from pieces of X-ray CT data for plural ROIs obtained by injecting a contrast medium or a tracer. Then, perfusion parameters of the respective ROIs are calculated by various algorithms based on the produced TDCs.

The perfusion parameters obtained as a result of the perfusion analysis are separated by colors according to the data values and displayed as a color map as shown in FIG. 2.

However, the color map that is a conventional display method of a result of the perfusion analysis is to display a result including pieces of perfusion data at all time phases non-dynamically. That is, the color map displays a result of overlapping all pieces of the perfusion data obtained from an object in the time axis direction.

Therefore, there is a problem that it becomes difficult to understand a blood flow dynamic state intuitively since information in the perfusion data such as how from which direction blood flow flows cannot be observed over time.

SUMMARY OF THE INVENTION

The present invention has been made in light of the conventional situations, and it is an object of the present invention to provide an X-ray CT apparatus, and a medical image processing apparatus and a medical image processing method that can display a result of blood flow perfusion analysis acquired from an object as information with time.

The present invention provides an X-ray CT apparatus comprising: a perfusion data acquisition unit configured to generate perfusion data of an object based on X-ray detection data detected by exposing an X-ray to the object with injecting contrast medium into the object; a perfusion parameter calculating unit configured to calculate perfusion parameters corresponding to plural regions of interest respectively based on time variations in density of the contrast medium for the plural regions of interest, the time variations being obtained from the perfusion data, the perfusion parameters being parameters with regard to time; and a perfusion parameter display unit configured to divide a period to be a calculation target of the time variations into plural time ranges and sequentially display images each including the regions of interest, the images corresponding to the time ranges and mutually different time phases respectively and being masked so as to make only regions of interest at which the perfusion parameters show values displayed, in an aspect to achieve the object.

The present invention also provides a medical image processing apparatus comprising: a perfusion data acquisition unit configured to acquire perfusion data of an object from an image diagnostic apparatus; a perfusion parameter calculating unit configured to calculate perfusion parameters corresponding to plural regions of interest respectively based on time variations in data values for the plural regions of interest, the time variations being obtained from the perfusion data, the perfusion parameters being parameters with regard to time; and a perfusion parameter display unit configured to divide a period to be a calculation target of the time variations into plural time ranges and sequentially display images each including the regions of interest, the images corresponding to the time ranges and mutually different time phases respectively and being masked so as to make only regions of interest at which the perfusion parameters show values displayed, in an aspect to achieve the object.

The present invention also provides a medical image processing method comprising: acquiring perfusion data of an object from an image diagnostic apparatus; calculating perfusion parameters corresponding to plural regions of interest respectively based on time variations in data values for the plural regions of interest, the time variations being obtained from the perfusion data, the perfusion parameters being parameters with regard to time; and dividing a period to be a calculation target of the time variations into plural time ranges and sequentially displaying images each including the regions of interest, the images corresponding to the time ranges and mutually different time phases respectively and being masked so as to make only regions of interest at which the perfusion parameters show values displayed, in an aspect to achieve the object.

The X-ray CT apparatus, and the medical image processing apparatus and the medical image processing method as described above can display a result of blood flow perfusion analysis acquired from an object as information with time.

DESCRIPTION OF THE PREFERRED EMBODIMENTS

An X-ray CT apparatus, and a medical image processing apparatus and a medical image processing method according to embodiments of the present invention will be described with reference to the accompanying drawings.
(Configuration and Function)

Figure 3:
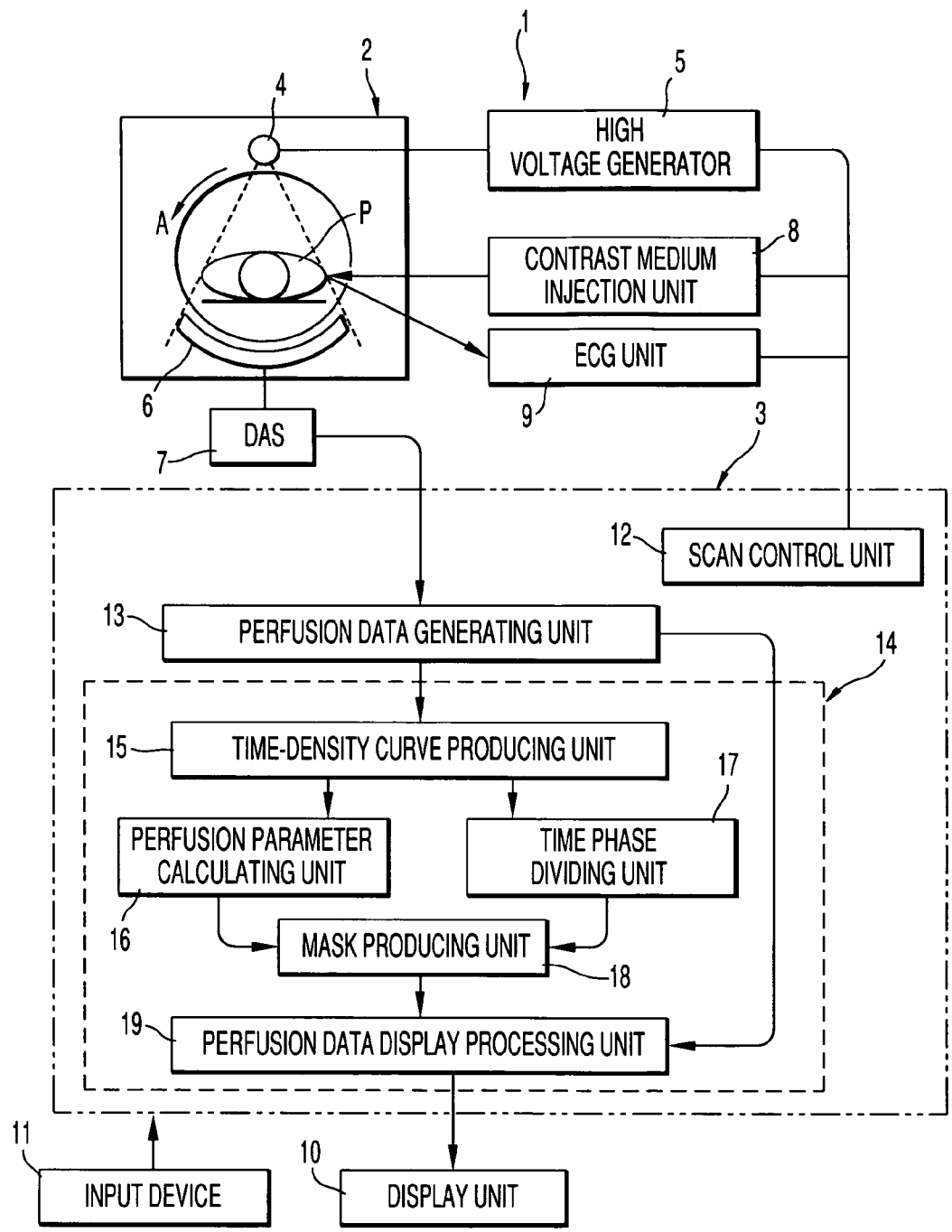
FIG. 3 is a block diagram showing an embodiment of an X-ray CT apparatus according to the present invention.

FIG. 3 is a block diagram showing an embodiment of an X-ray CT apparatus according to the present invention.

An X-ray CT apparatus 1 includes a gantry 2 and a computer 3. The gantry 2 has an X-ray tube 4, a high voltage generator 5, an X-ray detector 6, a DAS (data acquisition system) 7, a contrast medium injection unit 8 and an ECG (electrocardiogram) unit 9. The X-ray tube 4 and the X-ray detector 6 are mounted at mutually opposite positions that place an object P inside a rotating ring (not shown) that rotates continuously at a high speed.

The contrast medium injection unit 8 is controlled by a control signal from the computer 3 and has a function to inject a contrast medium into an object P according to predetermined conditions. The ECG unit 9 is connected to electrodes attached to the object P. The ECG unit 9 has a function to detect an ECG signal from the object P through the electrodes, generate an electrocardiogram of the object P from the detected ECG signal and provide it to the computer 3.

The high voltage generator 5 is configured to provide a tube current having a predetermined tube voltage to the X-ray tube 4 according to a control signal from the computer 3 in synchronized with the ECG generated by the ECG unit 9 to expose the object P to an X-ray with a desired energy from the X-ray tube 4. The X-ray detector 6 has plural X-ray detection elements arranged two-dimensionally. Thus, X-rays that penetrated the object P from directions up to 360 degrees are detected by respective X-ray detection elements in the X-ray detector 6.

The DAS 7 has a function to generate pieces of projection data corresponding to the respective X-ray detection elements by DAS processing such as amplification, integral processing, A/D (analog to digital) conversion processing and logarithmic transformation processing to the pieces of X-ray detection data output from the respective X-ray detection elements in the X-ray detector 6 and a function to output the generated pieces of projection data to the computer 3.

The display unit 10 and the input device 11 are connected to the computer 3. The computer 3 also has various functions by making its storage device read program and performing the program in its operation unit. Note that, circuits having corresponding functions may be provided instead of providing the functions with the computer 3. Specifically, the computer 3 has a function to obtain perfusion data of a blood flow of the object P from the projection data obtained from the X-ray detector 6 through the DAS 7 and a function to display temporal information of the obtained perfusion data on the display unit 10.

For that purpose, the computer 3 functions as a scan control unit 12, a perfusion data generating unit 13 and a medical image processing apparatus 14. The medical image processing apparatus 14 includes a time-density curve producing unit 15, a perfusion parameter calculating unit 16, a time phase dividing unit 17, a mask producing unit 18 and a perfusion data display processing unit 19.

The scan control unit 12 has a function to provide control signals to the gantry driving system in the gantry 2 for rotating the X-ray tube 4 and the X-ray detector 6, the high voltage generator 5 and the contrast medium injection unit 8 to control them based on an ECG from the ECG unit 9 according to a scan condition.

The perfusion data generating unit 13 has a function to generate contrast-enhanced X-ray CT image data as perfusion data of a blood flow using projection data that is output data from the DAS 7. The perfusion data is generated as dynamic contrast X-ray CT image data showing CT values or values obtained from the CT values at each time phase in respective ROIs corresponding to a blood flow part. One pixel or adjacent plural pixels of image data can be also set to a single ROI. When each pixel is set as a ROI, it becomes possible to display more microscopic detailed dynamic state of a blood flow.

The medical image processing apparatus 14 has a function to calculate perfusion parameters regarding time from perfusion data for each ROI generated in the perfusion data generating unit 13 and display the image data masked so that only ROIs in which a perfusion parameter shows a value in a certain range of duration are depicted selectively on the display unit 10 sequentially with changing the range of duration.

For that purpose, the time-density curve producing unit 15 has a function to obtain dynamic contrast CT image data for plural time phases of CT values or values obtained from the CT values for each ROI obtained in the perfusion data generating unit 13 and generate a TDC in each ROI based on the dynamic contrast CT image data.

Note that, a filter such as a quantum noise reduction filter may be applied to image data used for producing the TDCs for reducing noise in the image data. In addition, a curve approximation of a TDC may be performed using a spline interpolation or a γ function for smoothing of the TDC. Additionally, the processing that extracts only part where the perfusion parameter should be calculated may be performed to the dynamic contrast CT image data prior to calculation of the TDCs for reducing data processing amount. In this case, a method such as dynamic contour method or region growing method is known as a data extraction method.

The perfusion parameter calculating unit 16 has a function to calculate a perfusion parameter regarding time in each ROI based on the TDCs obtained from the time-density curve producing unit 15. Examples of perfusion parameter regarding time include a parameter that can be calculated over time and has time as a value like a TTP (time to peak) etc.

The time phase dividing unit 17 has a function to produce time ranges corresponding to plural time phases by dividing a period to be a calculation target of the TDCs obtained from the time-density curve producing unit 15 by a certain time range (interval) predetermined arbitrarily.

The mask producing unit 18 has a function to obtain time range information corresponding to the plural time phases from the time phase dividing unit 17 and the perfusion parameters such as TTPs in the respective ROIs from the perfusion parameter calculating unit 16 respectively and produce mask information for masking time ranges, except a time range where a value of the perfusion parameter such as a TTP exists, out of time ranges corresponding to the plural time phases. That is, the mask producing unit 18 has a function to produce a mask for extracting only ROIs where the perfusion parameter has values in a specific time range in the case of producing image data including the plural ROIs for the respective time ranges. The mask has only to be what is easily visible by a user and either a color mask or a black and white mask is acceptable.

The perfusion data display processing unit 19 has a function to generate pieces of mask image data for the respective plural time ranges using the masks for the respective plural time ranges produced in the mask producing unit 18 and display the generated plural time-series pieces of mask image data on the display unit 10 subsequently. The time-series mask image data becomes dynamic image data that temporally identifies ROIs where values of the perfusion parameter exist in each time range (each time phase) since the masks are produced so that the only time ranges and ROIs when and where the perfusion parameter shows values are extracted selectively. Therefore, a user becomes possible to easily observe ROIs where values of the perfusion parameter exist in each time range.

Figure 4:
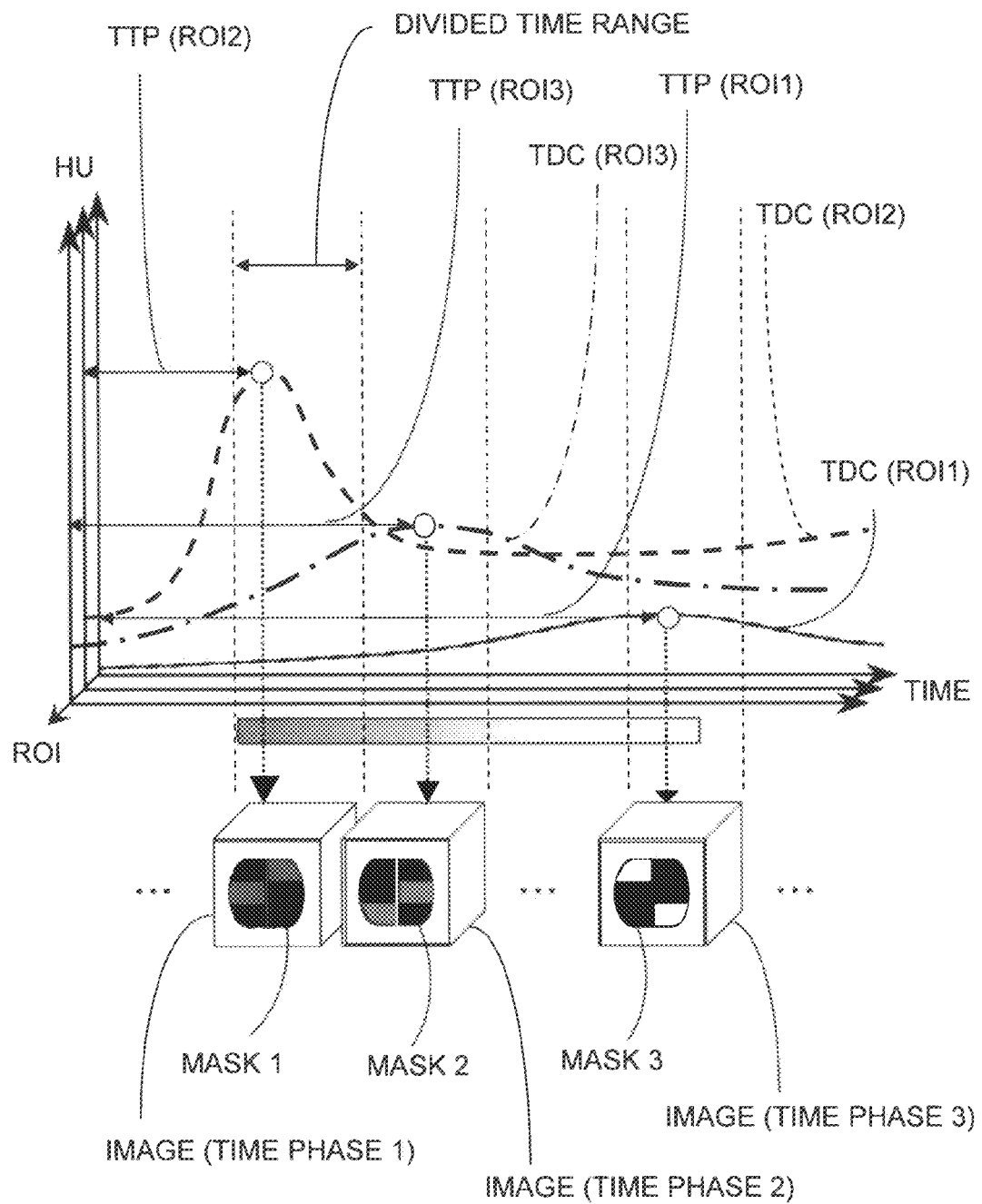
FIG. 4 is a diagram explaining a method for generating time series mask image data by the medical image processing apparatus shown in FIG. 3.

FIG. 4 is a diagram explaining a method for generating time series mask image data by the medical image processing apparatus 14 shown in FIG. 3.

In each graph of FIG. 4, the ordinate axis denotes a CT value (HU) corresponding to a density of contrast medium injected into an object P, the abscissa denotes time and the oblique axis denotes the ROI direction formed by mutually different ROIs. The respective curves in FIG. 4 represent TDC (ROIi) in N ROIs (ROI1, ROI2, ROI3, . . . , ROI N) (i is a natural number not over N).

As shown in FIG. 4, TDCs (TDC (ROI1), TDC (ROI2), TDC (ROI3), . . . , TDC (ROIN)) for the respective ROIs are produced in the time-density curve producing unit 15. Meanwhile, TTPs (TTP (ROI1), TTP (ROI2), TTP (ROI3), . . . , TTP (ROIN)) for the respective ROIs are calculated as the perfusion parameters in the perfusion parameter calculating unit 16. Further, the period to be a calculation target of the respective TDCs is divided into certain time ranges "DIVIDED TIME RANGE" by the time phase dividing unit 17.

Next, the mask information MASK1, MASK2, MASK3, . . . for masking ROIs other than ROIs where TTPs exist in each time range are produced for each time range in the mask producing unit 18. For example, the mask corresponding to the time range where the TTP of the ROI1 exists becomes MASK3 for extracting the ROI1. Then, the perfusion data display processing unit 19 produces time-series plural pieces of mask image data IMAGE (TIME PHASE 1), IMAGE (TIME PHASE 2), IMAGE (TIME PHASE 3), . . . respectively corresponding to the plural time phases TIME PHASE 1, TIME PHASE 2, TIME PHASE 3, . . . by using the masks MASK1, MASK2, MASK3, . . . , for the respective plural time ranges, produced in the mask producing unit 18.

Note that, the mask image data is displayed with mutually different colors corresponding to the respective time phases in the example shown in FIG. 4 since the different colors are assigned for the respective time ranges. As mentioned above, the perfusion parameter such as TTP can be displayed using a color scale. Alternatively, the perfusion parameter may be also displayed by brightness with a grayscale.

The perfusion data display processing unit 19 also has a function to perform display processing of the mask image data generated as mentioned above. For example, the mask image data can be subjected to a variety of display processing such as display processing so that the time-series plural pieces of mask image data are displayed over time with leaving afterimages, a display processing for performing switch display of the plural pieces of mask image data without leaving afterimages, display processing for temporally smooth dynamic displaying by interpolation processing between temporally adjacent two pieces of mask image data to produce intermediate mask image data, display processing for display with overlaying or synchronizing the mask image data with three-dimensional X-ray CT image data and/or display processing for display with overlaying or synchronizing subtraction image data between temporally adjacent pieces of three-dimensional X-ray CT image data with the mask image data. Especially, the subtraction image data between pieces of three-dimensional X-ray CT image data becomes image data which enhances a blood vessel. Therefore, the effect that it becomes to be able to understand how blood flows to a tissue can be expected if subtraction image data is displayed in synchronized with the mask image data.

It is practical to generate not time-series pieces of two-dimensional mask image data for only one slice but time-series pieces of three-dimensional mask image data for plural ROIs set three-dimensionally and display two-dimensional images generated by image processing such as multi-planar reconstruction processing on the display unit 10. The image processing such as multi-planar reconstruction processing can be also performed in the perfusion data display processing unit 19.

(Operation and Action)

Then, the operation and action of the X-ray CT apparatus 1 will be described.

Figure 1:
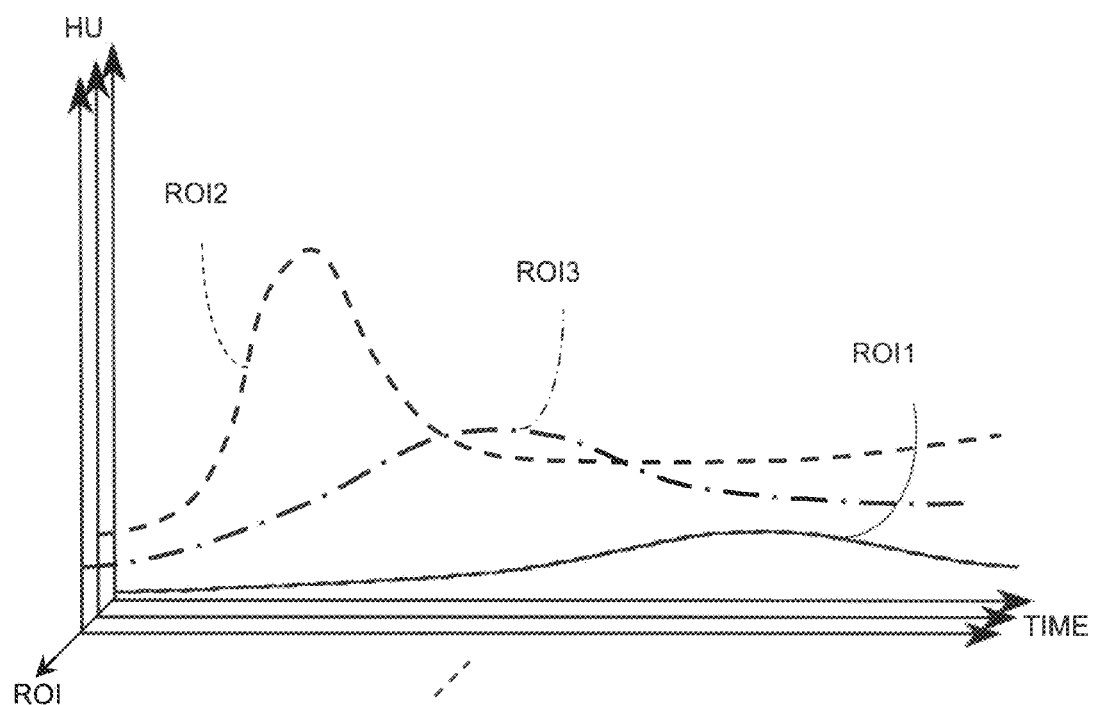
FIG. 1 shows conventional graphs indicating TDCs (time density curves) of contrast medium obtained as a result of perfusion analysis.
Figure 2:
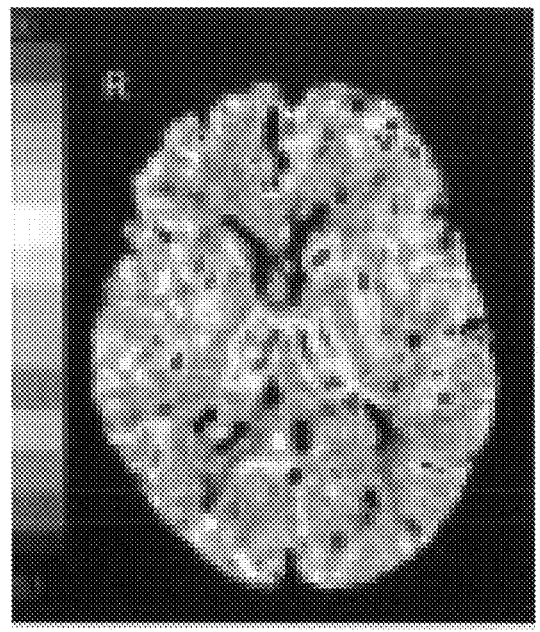
FIG. 2 is an image showing a method of displaying a perfusion analysis result obtained as the TDCs as shown in FIG. 1.
Figure 5:
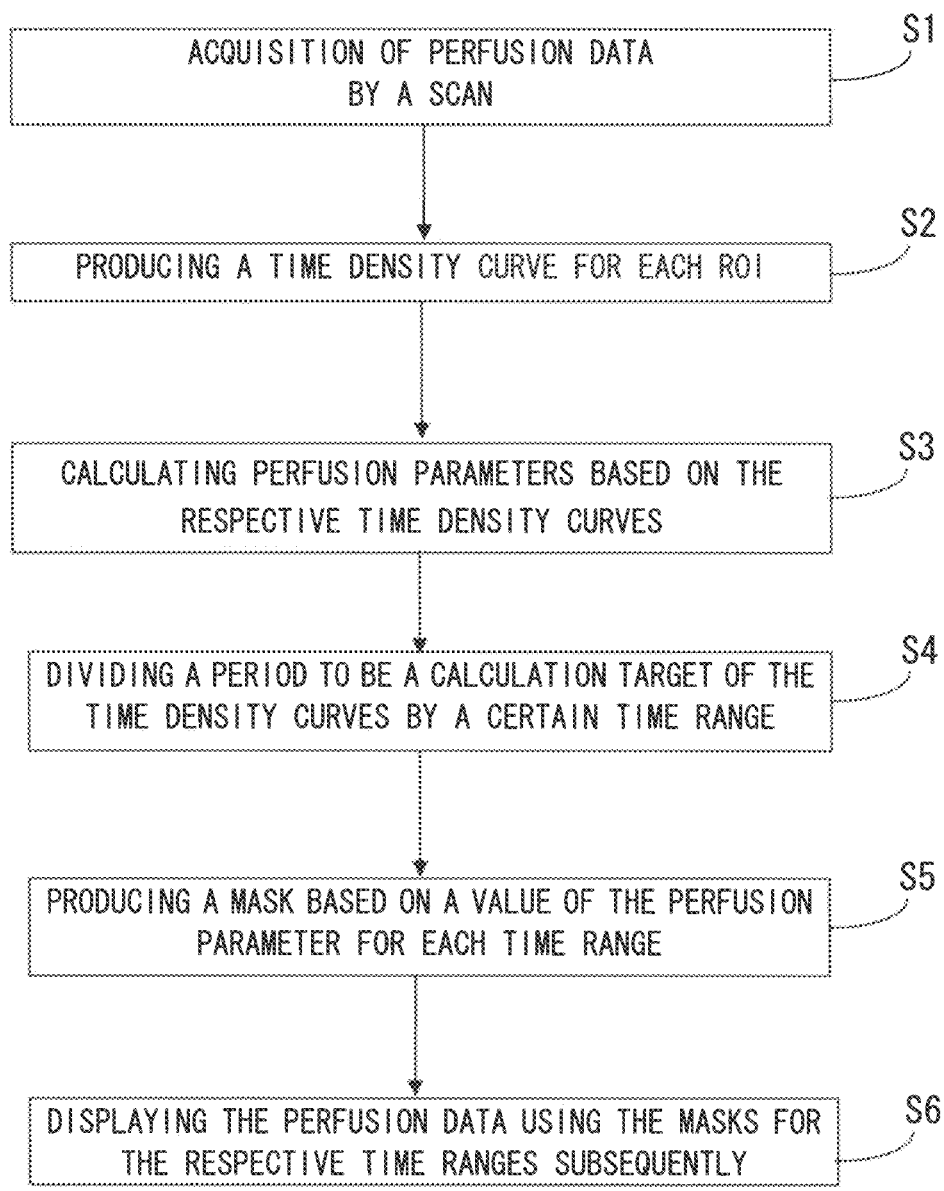
FIG. 5 is a flowchart showing a flow for acquiring pieces of perfusion data for plural ROIs in an object and sequentially displaying plural time series pieces of mask image data each displaying only ROIs involving TTPs with discrimination as information with time by the X-ray CT apparatus shown in FIG. 1.

FIG. 5 is a flowchart showing a flow for acquiring pieces of perfusion data for plural ROIs in an object P and sequentially displaying plural time series pieces of mask image data each displaying only ROIs involving TTPs with discrimination as information with time by the X-ray CT apparatus 1 shown in FIG. 1. The symbols each including S with a number in FIG. 5 indicate respective steps of the flowchart.

First, in step S1, perfusion data of the object P is acquired by a scan. That is, contrast medium is injected into the object P from the contrast medium injection unit 8 under a control signal from the scan control unit 12. Meanwhile, the X-ray tube 4 and the X-ray detector 6 rotate around the object P under a control signal from the scan control unit 12 based on an ECG signal detected in the ECG unit 9 and tube current is supplied to the X-ray tube 4 from the high voltage generator 5 in synchronized with the ECG signal. Therefore, X-rays are exposed to the object P from the X-ray tube 4 and the X-rays that penetrated the object P are detected by X-ray detection elements in the X-ray detector 6. The detected X-ray detection data is output to the DAS 7 and projection data is generated from the X-ray detection data. Then, the projection data is output to the computer 3.

Next, the perfusion data generating unit 13 in the computer 3 generates contrast X-ray CT image data as perfusion data of blood flow at respective time phases in respective ROIs from the projection data output from the DAS 7.

Next, in step S2, the time-density curve producing unit 15 in the medical image processing apparatus 14 produces TDCs in the respective ROIs based on the perfusion data.

Next, in step S3, the perfusion parameter calculating unit 16 calculates TTPs in the respective ROIs as perfusion parameters regarding time based on the TDCs in the respective ROIs.

Meanwhile, in step S4, the time phase dividing unit 17 divides a period to be a calculation target of the TDCs into specific time ranges. Consequently, plural time ranges corresponding to mutually different time phases are produced.

Next, in step S5, the mask producing unit 18 produces masks for extracting only ROIs where TTPs exist in a time range corresponding to each time phase.

Next, in step S6, the perfusion data display processing unit 19 generates plural pieces of mask image data, corresponding to the respective time phases, of which ROIs having no TTP are masked as temporal perfusion data information with using the masks for the respective time ranges produced in the mask producing unit 18 and displays the plural pieces of mask image data on the display unit 10 subsequently.

Figure 6:
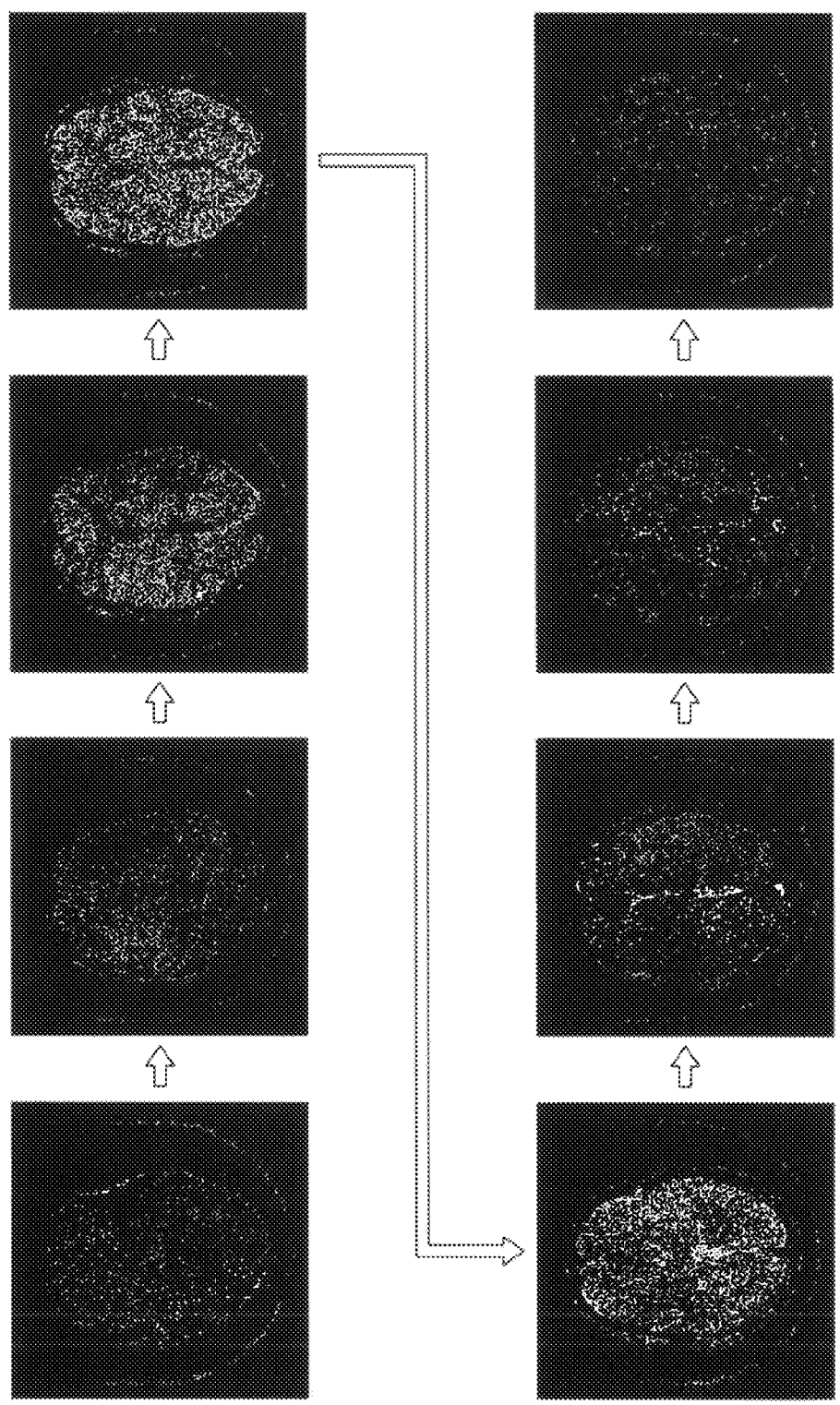
FIG. 6 shows an example of mask images corresponding to plural time phases displayed with time by the X-ray CT apparatus shown in FIG. 3.

FIG. 6 shows an example of mask images corresponding to plural time phases displayed with time by the X-ray CT apparatus 1 shown in FIG. 3.

The respective images in FIG. 6 are images at a same section in the head of the object P. As shown in FIG. 6, the plural pieces of mask image data representing the temporal perfusion data information can be displayed in the time phase order. FIG. 6 shows an example that respective pixels are set to ROIs respectively and an image is generated every second. As mentioned above, movements of blood flow between pixels can be displayed by dynamic display of the time-series pieces of mask image data. That is, a direction where blood flow flows can be observed visually based on movements of mask regions and non-mask regions by displaying the temporal mask image data.

The above-mentioned X-ray CT apparatus 1 is an apparatus which calculates perfusion parameters with time as data values such as TTPs based on TDCs, showing a result of perfusion analysis of a blood flow, obtained in respective ROIs of an object and makes it possible to observe a blood flow dynamic state over time by subsequently displaying images, masked so that only ROIs in which values of perfusion parameters are in a range of a certain duration are extracted selectively, with changing the range of the duration.

(Effect)

Therefore, the X-ray CT apparatus 1 makes it possible to observe a result of perfusion analysis over time. It also becomes easy to intuitively understand a blood flow dynamic state including a direction of a blood flow like from which direction the blood flow flows. Specifically, it is expected to become easy to recognize an area sustained by the collateral blood route in a region such as the head or the heart. In addition, it becomes possible to understand a charge vessel and a controlling area in an infarct more intuitively by displaying and overlaying subtraction image data between pieces of three-dimensional X-ray CT image data or three-dimensional dynamic X-ray CT image data with perfusion data such as TTPs corresponding to each time phase.

(Modifications)

In the embodiment described above, the example that the medical image processing apparatus 14, which generates and displays the image data showing a result of perfusion analysis over time from the perfusion data of the object P, is built in the X-ray CT apparatus 1 is described. However, the X-ray CT apparatus 1 can be also connected to the medical image processing apparatus 14 through a network. Further, the medical image processing apparatus 14 having a function to generate and display image data showing a result of perfusion analysis over time from perfusion data acquired in an image diagnostic apparatus, other than the X-ray CT apparatus 1, such as a MRI (Magnetic Resonance Imaging) apparatus, a nuclear medicine diagnostic apparatus (a PET (positron emission computed tomography) or SPECT (single photon emission computed tomography)) or an ultrasonic diagnostic apparatus can be built in the image diagnosis apparatus or connected with the image diagnosis apparatus through a network.

Further, in the embodiment described above, the example of using contrast medium is described. However, image data showing a result of perfusion analysis over time may be also generated from non-contrast perfusion data acquired without contrast medium. In this case, perfusion parameters regarding time can be calculated based on time change curves in signal intensities of acquisition data such as MR echo data showing the perfusion data.

What is claimed is:

1. An X-ray CT apparatus comprising:
an X-ray source configured to emit an X-ray;
an X-ray detector configured to detect the X-ray; and
a processing circuitry, wherein
the processing circuitry is configured to:
generate perfusion data of an object based on X-ray detection data detected by exposing the X-ray to the object with injecting contrast medium into the object;
calculate a perfusion parameter for each region of a plurality of regions of interest, each perfusion parameter including an elapse of time from a predetermined time to a time to peak of one of a plurality of time variations in density of the contrast medium obtained based on the perfusion data and each of the plurality of time variations corresponding to one region of interest of a plurality of regions of interest;
divide a period corresponding to the plurality of time variations into a plurality of divided time ranges;
determine, for each of the divided time ranges, a region of interest of the plurality of regions of interest whose corresponding perfusion parameter falls within the divided time range;
generate an image for each of the plurality of divided time ranges, the image for one of the plurality of divided time ranges showing only profusion data of the region of interest whose perfusion parameter falls within the one of the plurality of divided time ranges; and
sequentially display the images for each of the plurality of divided time ranges on a display unit.

2. The X-ray CT apparatus of claim 1, wherein the processing circuitry is configured to calculate the perfusion parameter for a specific region of interest of the plurality of regions of interest by setting each pixel in a focused region as the specific region of interest.

3. The X-ray CT apparatus of claim 1, wherein
the image for the one of the plurality of divided time ranges includes a plurality of indicating areas, and
the plurality of indicating areas includes:
an unmasked indicating area corresponding to the region of interest whose perfusion parameter falls within the one of the plurality of divided time ranges and being unmasked, and
a masked indicating area corresponding to regions of interest of the plurality of regions of interest whose perfusions parameters fall outside the one of the plurality of divided time ranges and being masked.

4. A medical image processing apparatus comprising a processing circuitry, wherein
the processing circuitry is configured to:
acquire perfusion data of an object from an image diagnostic apparatus;
calculate a perfusion parameter for each region of a plurality of regions of interest, each perfusion parameter including an elapse of time from a predetermined time to a time to peak of one of a plurality of time variations in density of the contrast medium obtained based on the perfusion data and each of the plurality of time variations corresponding to one region of interest of a plurality of regions of interest;
divide a period corresponding to the plurality of time variations into a plurality of divided time ranges;
determine, for each of the divided time ranges, a region of interest of the plurality of regions of interest whose corresponding perfusion parameter falls within the divided time range;
generate an image for each of the plurality of divided time ranges, the image for one of the plurality of divided time ranges showing only profusion data of the region of interest whose perfusion parameter falls within the one of the plurality of divided time ranges; and
sequentially display the images for each of the plurality of divided time ranges on a display unit.

5. The medical image processing apparatus of claim 4, wherein the processing circuitry is configured to calculate the perfusion parameter for a specific region of interest of the plurality of regions of interest by setting each pixel in a focused region as the specific region of interest.

6. The medical image processing apparatus of claim 4, wherein
the image for the one of the plurality of divided time ranges includes a plurality of indicating areas, and
the plurality of indicating areas includes:
an unmasked indicating area corresponding to the region of interest whose perfusion parameter falls within the one of the plurality of divided time ranges and being unmasked, and
a masked indicating area corresponding to regions of interest of the plurality of regions of interest whose perfusions parameters fall outside the one of the plurality of divided time ranges and being masked.

7. A medical image processing method comprising:
acquiring perfusion data of an object from a storage unit;
calculating a perfusion parameter for each region of a plurality of regions of interest, each perfusion parameter including an elapse of time from a predetermined time to a time to peak of one of a plurality of time variations in density of the contrast medium obtained based on the perfusion data and each of the plurality of time variations corresponding to one region of interest of a plurality of regions of interest;
dividing a period corresponding to the plurality of time variations into a plurality of divided time ranges;
determining, for each of the divided time ranges, a region of interest of the plurality of regions of interest whose corresponding perfusion parameter falls within the divided time range;
generating an image for each of the plurality of divided time ranges, the image for one of the plurality of divided time ranges showing only profusion data of the region of interest whose perfusion parameter falls within the one of the plurality of divided time ranges; and
sequentially displaying the images for each of the plurality of divided time ranges on a display unit.

8. The medical image processing method of claim 7, wherein the perfusion parameter calculating calculates the perfusion parameter for a specific region of interest of the plurality of regions of interest by setting each pixel in a focused region as the specific region of interest.

9. The medical image processing method of claim 7, wherein
the image for the one of the plurality of divided time ranges includes a plurality of indicating areas, and
the plurality of indicating areas includes:
an unmasked indicating area corresponding to the region of interest whose perfusion parameter falls within the one of the plurality of divided time ranges and being unmasked, and
a masked indicating area corresponding to regions of interest of the plurality of regions of interest whose perfusions parameters fall outside the one of the plurality of divided time ranges and being masked.

* * * * *